United States Patent

Plant Pat. 3,980
Patented Nov. 16, 1976

3,980

STRAWBERRY PLANT

Royce S. Bringhurst, Davis, and Victor Voth, Santa Ana, Calif., assignors to The Regents of the University of California, Berkeley, Calif.

Filed Oct. 23, 1975, Ser. No. 625,283
Int. Cl.[2] A01H *5/03*
U.S. Cl. Plt.—49 1 Claim

This invention relates to a new and distinct variety of strawberry plant designated as "Toro" which is the result of a cross between Cal. 37.20–45 and "Sequoia," U.S. Plant Pat. 3,178.

"Toro" fruited first and was selected at the Wolfskill Experimental Orchards at the University of California near Davis, Calif. in 1967. At that time it was designated Cal. 65.272–105.

"Toro" has been tested extensively at the various university facilities throughout the State of California under strict control. Meristem originated, virus-negative stock has been developed at the university, asexually reproduced and multiplied.

Figure 1:
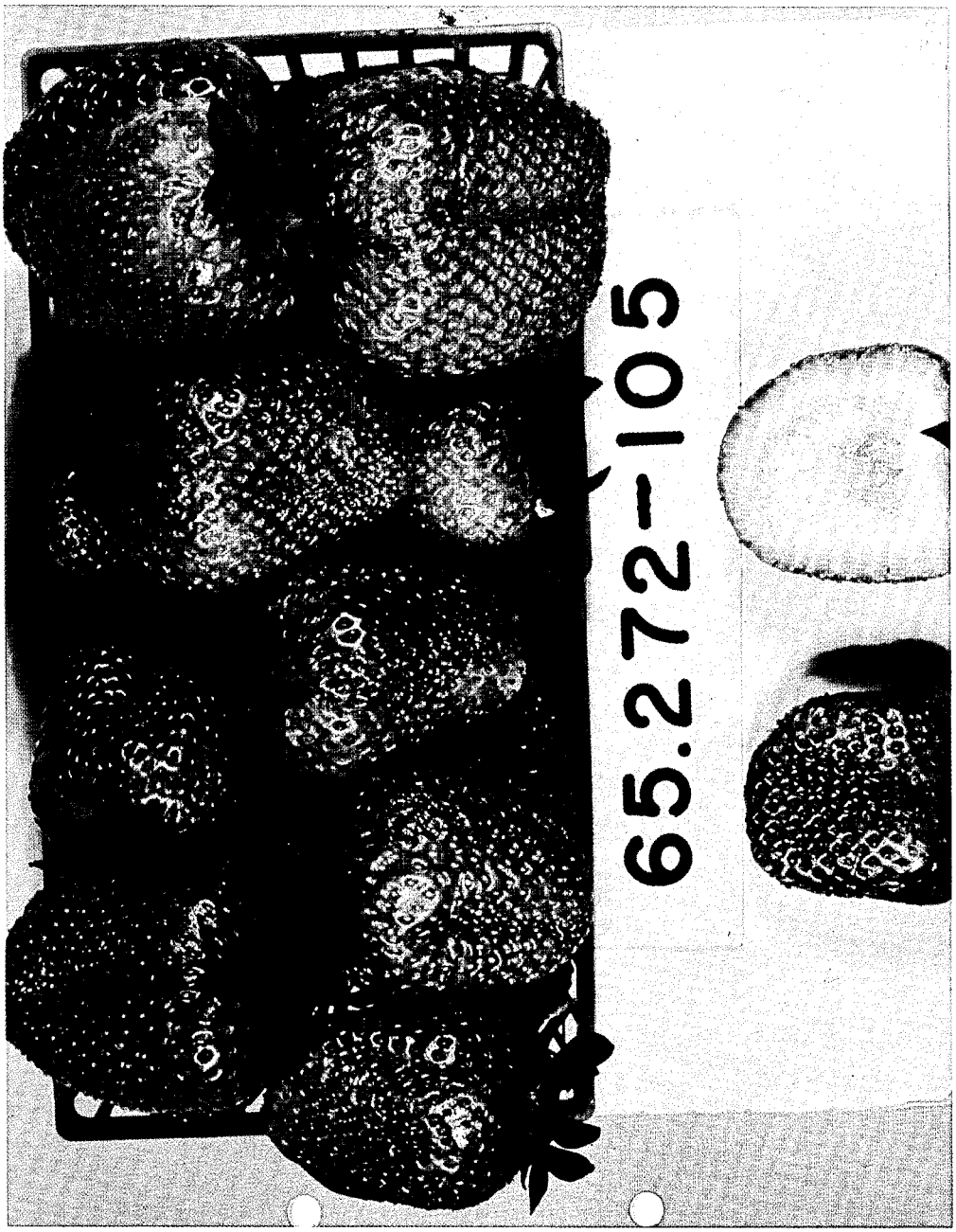
Figure 2:
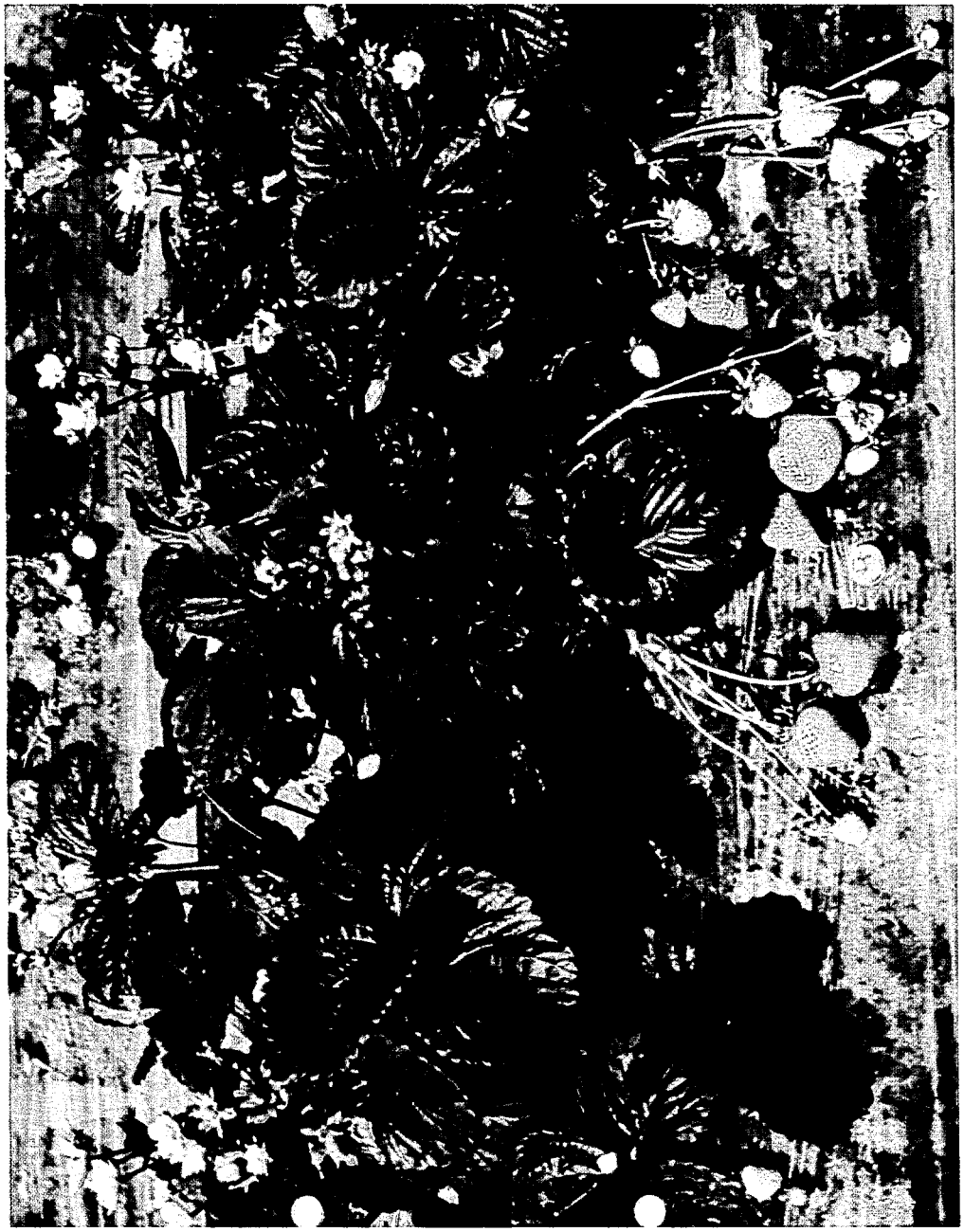

Typical plant, flower and fruit characteristics are presented in the accompanying photographic color reproductions in which FIG. 1 shows medium long conic fruit, one of which is in cross section and in which FIG. 2 shows typical springtime leaves, plant, flower and fruiting habit of winter planting in the southern areas of California.

Under optimum conditions, "Toro" may yield quantities of fruit comparable of what should be expected from "Tioga" or "Tufts," U.S. Plant Pat. 3,561, under the winter planting system. The advantage of the cultivar is earliness. With the summer planting system "Toro" yields considerably less than "Tioga" or "Tufts" under comparable conditions.

The dessert quality of "Toro" fruit is good with soluble solids about the same as "Tioga" and "Tufts" according to experimentation. "Toro" fruit is extremely high in ascorbic acid (vitamin C) in comparison with that of "Tioga" and "Tufts," that is, about 98 mg./100 grams of fresh fruit as compared with 48 mg./100 grams and 58 mg./100 grams of fresh fruit respectively for the latter two cultivars.

"Toro" is adapted and should be useful as an interim cultivar for winter planting in coastal areas where earliness is desirable, particularly in southern California, planted in early to mid-October. Relatively low yield will limit its usefulness in summer planting.

The varietal characteristics of this new strawberry plant described below in detail were observed upon its discovery and subsequently through its test period.

DESCRIPTION:

Plants

"Toro" plants are medium-large in size, erect in habit about the same as those of "Tioga" "Tufts" and "Sequoia." They are distinctive from other University of California cultivars in that the leaves are exceptionally dark and semi-glossy. "Toro" plants are about as vigorous as those of "Sequoia" and require about the same amount of nitrogen fertilization. "Toro" plants are about as tolerant of salinity as those of "Sequoia" and they are susceptible to Verticillium Wilt. "Toro" runners much less prolifically than most other University cultivars. It is about like "Aliso" in that respect and the runner plants are exceptionally large, an advantage in winter planting.

Flowering and flowers

"Toro" is a standard short-day type that commences flowering earlier than "Tufts" or "Tioga" in winter plantings.

Flowers are borne on medium-long panicles, somewhat shorter than those of "Tufts" but longer than those of "Tioga." Flowers are self-fruitful with an abundance of pollen and they almost always set well.

Fruit

The medium long conic fruit is round in cross section except for many of the primaries which tend to be wedged to double round. It is seldom malformed but primary fruits may be doubled with a tendency to split (claw) although this is not a persistent problem throughout the season.

The ripe color is bright red-orange that deepens to orange-red as it matures, distinctly lighter than fruit of "Tufts" or "Tioga" although it is attractive. Internally the color is much lighter than that of "Tioga," orange to whitish orange. The flesh is somewhat softer than that of "Tioga."

The skin is not as tough as that of "Tioga" but it will ship well if handled carefuly. It is more susceptible to rain damage than the skin of "Tufts" or "Tioga." The achenes are about flush with the surface, similar to "Tioga."

"Toro" fruit usually averages larger than that of "Tufts" although the size falls off as the harvest cycle advances, similar to "Tioga."

We claim:

1. The new and distinct variety of strawberry plant herein described and illustrated, and identified by the characteristics enumerated above.

No references cited.

ROBERT E. BAGWILL, Primary Examiner